US012601663B2

(12) United States Patent
Job et al.

(10) Patent No.: US 12,601,663 B2
(45) Date of Patent: Apr. 14, 2026

(54) GEOLOGICAL SAMPLE HOLDER

(71) Applicant: PlotLogic Pty Ltd, Queensland (AU)

(72) Inventors: Andrew Job, Queensland (AU);
Matthew Garlan, Queensland (AU);
Johann Wyss, Queensland (AU)

(73) Assignee: PlotLogic Pty Ltd, Red Hill (AU)

( * ) Notice: Subject to any disclaimer, the term of this
patent is extended or adjusted under 35
U.S.C. 154(b) by 322 days.

(21) Appl. No.: 18/278,375

(22) PCT Filed: Feb. 23, 2022

(86) PCT No.: PCT/AU2022/050138
§ 371 (c)(1),
(2) Date: Aug. 22, 2023

(87) PCT Pub. No.: WO2022/178576
PCT Pub. Date: Sep. 1, 2022

(65) Prior Publication Data
US 2024/0035936 A1 Feb. 1, 2024

(30) Foreign Application Priority Data
Feb. 24, 2021 (AU) ................................ 2021900500

(51) Int. Cl.
*B01L 3/00* (2006.01)
*E21B 25/00* (2006.01)
*G01N 1/28* (2006.01)
*G01N 1/36* (2006.01)
*G01N 33/24* (2006.01)

(52) U.S. Cl.
CPC ............. *G01N 1/36* (2013.01); *E21B 25/005*
(2013.01); *G01N 33/24* (2013.01)

(58) Field of Classification Search
CPC ... B01L 3/00; G01N 1/00; G01N 1/28; G01N
1/36; G01N 33/24; E21B 25/005
See application file for complete search history.

(56) References Cited

U.S. PATENT DOCUMENTS

| | | | |
|---|---|---|---|
| 2,015,522 A | 9/1935 | Hoffman | |
| 2,183,971 A | 12/1939 | Miller | |
| 3,420,443 A | 1/1969 | Van Koppen et al. | |
| 9,943,857 B1 | 4/2018 | Reed | |
| 2018/0093277 A1 | 4/2018 | Reed | |
| 2019/0224685 A1* | 7/2019 | Benenati | ................... B01L 9/56 |
| 2023/0003918 A1 | 1/2023 | Job et al. | |

FOREIGN PATENT DOCUMENTS

| | | | |
|---|---|---|---|
| AU | 2021103784 | 9/2021 | |
| CA | 2873528 | 6/2016 | |
| CN | 110261575 A * | 9/2019 | ............. G01N 33/24 |
| WO | WO 2021/108838 | 6/2021 | |
| WO | WO | 9/2022 | |
| | PCT/AU2022/050138 | | |

OTHER PUBLICATIONS

Machine Translation of CN-110261575-A (Year: 2019).*

* cited by examiner

*Primary Examiner* — Nguyen Q. Ha
(74) *Attorney, Agent, or Firm* — Wells St. John P.S.

(57) ABSTRACT

The present invention relates to a geological sample holder.
The holder includes a container for containing a geological
sample and for orienting in an upright configuration. One or
more baffles extend across the container and baffle the
geological sample. Advantageously, the sample holder may
be angled to the horizontal for scanning, and the baffles
baffle the geological sample from shifting downwards.

19 Claims, 2 Drawing Sheets

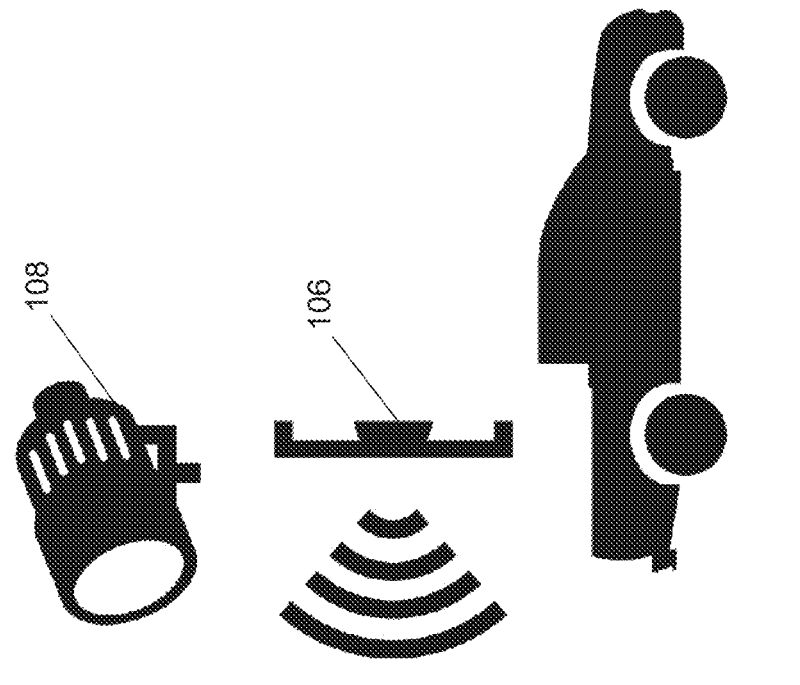
108
106
FIG. 1
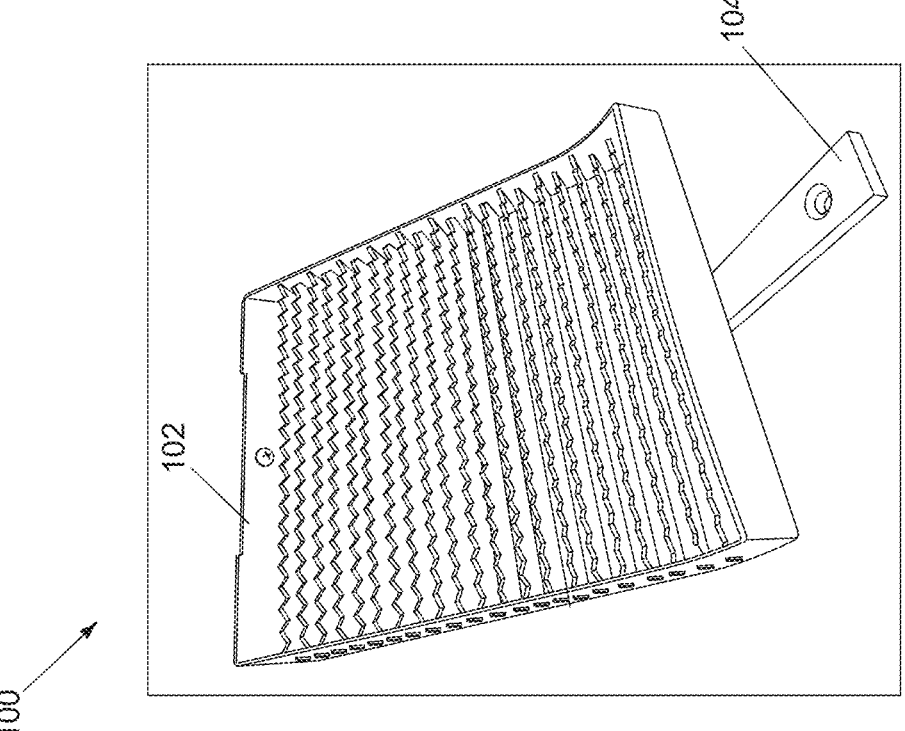
100
102
104

GEOLOGICAL SAMPLE HOLDER

RELATED PATENT DATA

This application is a 35 U.S.C. § 371 of and claims priority to PCT International Application Number PCT/AU2022/050138, filed 23 Feb. 2022, which was published in English, and which claims priority to AU patent application serial no. 2021900500, filed 24 Feb. 2021, the teachings of which are incorporated herein by reference.

TECHNICAL FIELD

The present invention relates to a geological sample holder.

BACKGROUND

The reference to any prior art in this specification is not, and should not be taken as an acknowledgement or any form of suggestion that the prior art forms part of the common general knowledge.

PCT/AU2020/051275 discloses a mobile mining spectral scanner for detecting changes in the ore grade of a rock face in near real time. In practice, such spectral scanners are calibrated before use. Invariably, it is also desirable to validate the performance of a material characterization algorithm. To this end, small plates of known spectral reflectance properties, such as Spectralon®, have been used to provide near vertical scanning of targets.

Problems with such technology include (1) the cost to manufacture known reflectance targets is high; (2) these targets are difficult to deploy in non-laboratory conditions, as they are no longer calibrated once they get small amounts of dust/dirt on them; and (3) the panels provide only a way to calibrate the sensor characteristics and atmospheric correction algorithms used for field scanning.

The preferred embodiment provides an improved system for calibrating and/or validating algorithms of a mobile mining scanner.

SUMMARY OF THE INVENTION

According to one aspect of the present invention, there is provided a geological sample holder for use in scanning, the holder including:
  a container for containing a geological sample and for orienting in an upright configuration during scanning; and
  baffles extending across the container and for baffling the geological sample to restrain the geological sample from shifting downwards and mimic a rock wall of a mine.

Advantageously, the sample holder may be angled to the horizontal for scanning, and the baffles baffle the geological sample from shifting downwards.

Each baffle may include an uneven edge. Preferably, the edge is a top or free edge. Preferably, the uneven edge includes an undulating edge. The undulating edge may be serrated or pointed. The baffles may include two types of baffles, alternatingly arranged along the container. Adjacent undulating edges may be staggered. Each baffle may be straight, and the baffles may be parallel. In use, the baffles may extend horizontally.

Each undulating edge may include peaks and troughs, the peaks and troughs collectively being mis-aligned with the container.

The container may include a base, and one or more sloping ends extending from the base. Each end may extend at between 115° and 165°, and preferably about 135° from the base. At least one of the ends may define a mounting formation. The base may include fastening formations to facilitate fastening with the baffles.

The container may include a pair of sides extending from a base. The sides may include fastening formations to facilitate fastening with the baffles.

According to a preferred embodiment, there is provided a geological sample system inducing:
  the geological sample holder; and
  a mount for mounting the sample holder relative to a scanner.

The scanner may be a mobile scanner, and the sample holder may be upright to advantageously provide for improved calibration and/or algorithm validation of the scanner. The upright geological sample holder may be at an angle of at least 45°, at least 70°, and preferably at about 80° from horizontal.

The system may include the scanner for scanning the geological sample in the mounted sample holder. The scanner may scan horizontally. The scanner may include a spectral scanner. The system may include a light source for lighting the geological sample being scanned.

According to another aspect of the present invention, there is provided a geological sample analysis method, the method involving:
  orienting a geological sample holder, holding a geological sample, in an upright configuration, the holder including baffles for baffling the geological sample to restrain the geological sample from shifting downwards and mimic a rock wall of a mine; and
  scanning the geological sample in the upright geological sample holder.

Any of the features described herein can be combined in any combination with any one or more of the other features described herein within the scope of the invention.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 1 is a schematic view of a geological sample scanning system in accordance with an embodiment of the present invention.

DETAILED DESCRIPTION OF PREFERRED EMBODIMENTS

Figure 2:
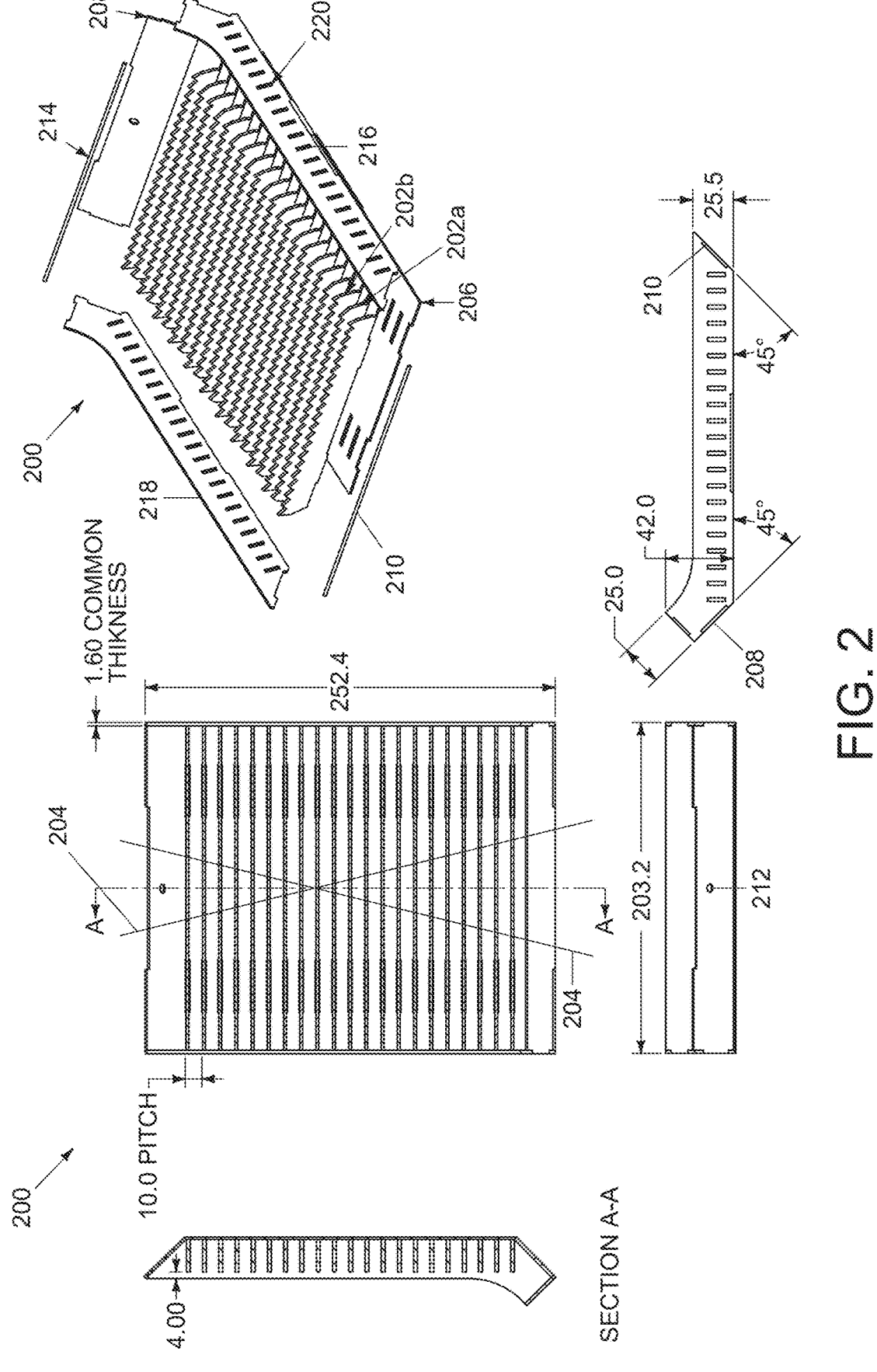
FIG. 2 is an orthographic drawing of a geological sample holder of the system of FIG. 1, where all dimensions are in millimeters.

According to an embodiment of the present invention, there is provided a geological sample scanning system 100 as shown in FIG. 1. The system 100 includes a geological sample holder 102, and an elbow mount 104 for mounting the sample holder 102 relative to a spectral scanner 106.

The scanner 106 is a mobile scanner of the type described in PCT/AU2020/051275, incorporated herein by reference. The sample holder 102 is oriented upright to advantageously provide for improved calibration and/or algorithm validation of the scanner 106. In use, the upright geological sample holder 102 is oriented at an angle of about 80° from horizontal.

The system 100 also includes the scanner 106 for scanning the geological sample, in the form of crushed rock, located in the mounted sample holder 102. The scanner 106 scans horizontally and a light source 108 is provided for lighting the geological sample being scanned.

Turning to FIG. 2, the geological sample holder 102 includes an upright tray container 200 for containing the geological sample. A series of baffles 202 extend across the container 200 and baffle or restrain the geological sample from shifting during scanning. The sample holder 102 is angled to the horizontal for scanning, and the straight baffles 202 extend horizontally to prevent the geological sample from shifting downwards.

Each baffle 202 includes an uneven top or free edge to facilitate effective scanning and minimise the amount of tray material that can skew results. The uneven edge is preferably an undulating edge that is serrated or pointed. The baffles 202 include two types of baffles 202a, 202b, alternatingly arranged in parallel along the container 200 so that adjacent undulating edges are staggered. Each undulating edge includes peaks and troughs, and the peaks and troughs are collectively mis-aligned with the container 200 as generally shown along example lines 204 (and parallel lines not shown).

The container 200 includes a plate base 206, and two sloping ends 208, 210 extending from the base 206. Each end 208, 210 extend at about 135° from the base, and at least one end 208 defines a mounting hole 212 (i.e. formation) for receiving a fastener when fastening to the elbow mount 104. A retainer plate 214 is mounted transverse the lower end 208 to retain any spillage of the geological sample.

The container 200 also includes a pair of sides 216, 218 extending from the base 206. The base 206 and the sides 216, 218 include fastening slot formations 220 to facilitate fastening with the baffles 202 which are inserted therein.

In practice, when calibrating and/or validating algorithms of the scanner 106, the geological material is packed into the container 200 between the baffles.

The sample holder 102 is then mounted to elbow mount 104 so as to be upright.

The mobile scanner 106 can then be used in its normal configuration, as it would be used in the field, to scan the upright sample holder 102 which mimics a rock wall of a mine. The scanner 106 can be readily calibrated and its algorithms validated, before actual use in the mine.

The upright sample holder 102 ameliorates at least some of the disadvantages of the prior art by also providing: (1) a low cost way of conducting calibrated panel testing in the field; (2) a robust and reliable method that can be deployed in hostile environments, such as on active mine sites; (3) a method for testing material characterization algorithms, in the field, to validate the performance and accuracy of these algorithms, by comparing the algorithm results against know material properties of the sample, such as geochemical assay results for ore grade.

For example, the sample holder 102 allows the direct comparison between hyperspectral imaging algorithms for classification of ore grade of material in the field in near vertical conditions, and comparing directly with geochemical assay to provide, inter alia, a method for validating the % accuracy of the classification algorithm.

The holders 102 are suitable for use in situations where the natural angle of repose for a crushed, or powdered, sample of the geological material is less than the angle required to simulate scanning conditions likely encountered in a range of field-based applications, such as scanning of a near vertical rock face. Simulation of scanning angles that are not perfectly nadir to the light source 108 and scanning sensor 106 is important for routine calibration of sensor performance and algorithm validation.

The holder 102 allows the dust sample to be tilted to an angle that is beyond a nadir angle to the input light source 108 and scanning sensor 106, and also beyond the material's natural angle of repose. This system 100 allows for a material to be scanned from many different angles to both a light source 108 and a scanning sensor 106.

A person skilled in the art will appreciate that many embodiments and variations can be made without departing from the ambit of the present invention.

For example, the skilled person will appreciate that the holders 102 are scalable for different sample sizes.

In compliance with the statute, the invention has been described in language more or less specific to structural or methodical features. It is to be understood that the invention is not limited to specific features shown or described since the means herein described comprises preferred forms of putting the invention into effect.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The invention claimed is:

1. A geological sample holder for use in scanning, the holder including:
   a container for containing a geological sample and for orienting to a configuration that is upright or angled relative to a horizontal during scanning, the container including a base not including arrays of air perforations between baffles, the base including fastening formations to facilitate fastening with the baffles; and
   the baffles extending across the container and for baffling the geological sample to restrain the geological sample from shifting downwards and mimic a rock wall of a mine.

2. A geological sample holder as claimed in claim 1, wherein the sample holder is angled relative to the horizontal for scanning.

3. A geological sample holder as claimed in claim 1, wherein each baffle includes an uneven edge.

4. A geological sample holder as claimed in claim 3, wherein the edge is a top or free edge.

5. A geological sample holder as claimed in claim 3, wherein the uneven edge includes an undulating edge.

6. A geological sample holder as claimed in claim 5, wherein the undulating edge is serrated or pointed.

7. A geological sample holder as claimed in claim 5, wherein each undulating edge includes peaks and troughs, the peaks and troughs collectively being mis-aligned with a central axis of the container.

8. A geological sample holder as claimed in claim 5, wherein adjacent undulating edges are staggered.

9. A geological sample holder as claimed in claim 1, wherein the container includes one or more sloping ends extending from the base, each end extending at between 115° and 165°, and preferably about 135° from the base.

10. A geological sample holder as claimed in claim 9, wherein at least one of the ends define a mounting formation.

11. A geological sample holder as claimed in claim 1, wherein the container includes a pair of sides extending from a base, the sides including fastening formations to facilitate fastening with the baffles.

12. A geological sample system including:

a geological sample holder for use in scanning, the holder including:

a container for containing a geological sample and for orienting to a configuration that is upright or angled relative to a horizontal during scanning; and baffles extending across the container and for baffling the geological sample to restrain the geological sample from shifting downwards and mimic a rock wall of a mine, wherein the geological sample holder is oriented to the configuration; and a scanner for scanning the geological sample in the geological sample holder.

13. A geological sample system as claimed in claim 12, further including a mount for mounting the sample holder relative to the scanner.

14. A geological sample system as claimed in claim 12, wherein the scanner is a mobile scanner, and the sample holder advantageously provides for improved calibration and/or algorithm validation of the scanner.

15. A geological sample system as claimed in claim 12, wherein the geological sample holder is positioned at an angle of at least 45°, at least 70°, and preferably at about 80° from the horizontal.

16. A geological sample system as claimed in claim 12, wherein the scanner scans horizontally and includes a spectral scanner.

17. A geological sample system as claimed in claim 12, further including a light source for lighting the geological sample being scanned.

18. A geological sample analysis method using the system of claim 12, the method including:

orienting the geological sample holder, holding the geological sample, to the configuration that is upright or angled relative to a horizontal, the holder including the baffles for baffling the geological sample to restrain the geological sample from shifting downwards and mimic a rock wall of a mine; and scanning the geological sample in the geological sample holder.

19. A geological sample holder for use in scanning, the holder including:

a container for containing a geological sample and for orienting to a configuration that is upright or angled relative to a horizontal during scanning, the container including a base not including arrays of air perforations between baffles, the container including one or more sloping ends extending from the base, each end extending at between 115° and 165°, and preferably about 135° from the base; and the baffles extending across the container and for baffling the geological sample to restrain the geological sample from shifting downwards and mimic a rock wall of a mine.

\* \* \* \* \*